United States Patent
Weitzel et al.

(10) Patent No.: US 6,709,414 B2
(45) Date of Patent: *Mar. 23, 2004

(54) SYSTEM FOR DETERMINING BLOOD FLOW RATE IN A VESSEL USING DIVERTED FLOW MEASUREMENTS

(75) Inventors: William F. Weitzel, Ypsilanti, MI (US); Jonathan M. Rubin, Ann Arbor, MI (US); Joseph M. Messana, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/372,470

(22) Filed: Feb. 21, 2003

(65) Prior Publication Data

US 2003/0167030 A1 Sep. 4, 2003

Related U.S. Application Data

(60) Division of application No. 09/310,673, filed on May 12, 1999, now Pat. No. 6,575,927, which is a continuation-in-part of application No. 09/160,685, filed on Sep. 25, 1998, now Pat. No. 6,167,765.

(51) Int. Cl.[7] ........................ A61M 37/00; C02F 1/44; G01F 1/20

(52) U.S. Cl. .................. 604/6.11; 604/5.04; 604/8; 604/9; 210/645; 210/646; 210/87; 73/861.18

(58) Field of Search ................ 73/861.18, 861.12, 73/861.15, 861.25, 202; 210/254, 646, 294, 790, 87, 85, 645, 90, 98, 103; 604/27, 28, 30, 5.01, 4.01, 5.04, 6.11, 6.09, 6.08, 8, 9, 10; 600/504, 454, 455, 456, 437

(56) References Cited

U.S. PATENT DOCUMENTS 3,559,482 A 2/1971 Baker et al.

(List continued on next page.)

FOREIGN PATENT DOCUMENTS

DE 195 28 907 C1 11/1996

OTHER PUBLICATIONS

C. Langescheid, et al., Anastomosis–Pressure–Dynamic Method for Determining AV Fistual Flood Flow Rate, Dialysis & Transplanta–tion, Jun. 1977, pp. 54–55.

(List continued on next page.)

*Primary Examiner*—Angela D. Sykes
*Assistant Examiner*—Leslie R Deak
(74) *Attorney, Agent, or Firm*—Brooks Kushman P.C.

(57) ABSTRACT

A system and method are provided for determining the performance of a vessel, such as a hemodialysis access, which communicates blood between two locations of a patient. A conduit, such as an external dialysis circuit or an intravascular catheter, is provided in fluid communication with the vessel, and has a diversion point for diverting blood from the vessel into the conduit. The system further includes means for determining a flow rate of the diverted blood through the conduit. A first sensor in communication with the vessel generates at least one signal that is a function of a blood flow rate in the vessel downstream from the diversion point, wherein the downstream flow rate depends on the determined conduit flow rate and the performance of the vessel can be determined based on the signal. In addition, a processor can be provided in communication with the first sensor for determining a flow rate in the vessel upstream from the diversion point from the signal and the conduit flow rate. In a preferred embodiment, the first sensor is an ultrasonic sensor, and the at least one signal represents a time-averaged mean Doppler velocity of blood flow. Still further, additional sensors may be employed to provide a measure of the upstream flow rate as well as the conduit flow rate.

32 Claims, 6 Drawing Sheets

U.S. PATENT DOCUMENTS

| | | | |
|---|---|---|---|
| 4,041,757 | A | 8/1977 | Baker et al. |
| 4,315,431 | A | 2/1982 | Hawk |
| 4,391,148 | A | 7/1983 | Sainz et al. |
| 4,454,758 | A | 6/1984 | Miller |
| 5,092,836 | A | 3/1992 | Polaschegg |
| 5,203,337 | A | 4/1993 | Feldman |
| 5,297,426 | A | 3/1994 | Kane et al. |
| 5,312,550 | A | 5/1994 | Hester |
| 5,333,496 | A | 8/1994 | Fenelon |
| 5,333,614 | A | 8/1994 | Feiring |
| 5,505,204 | A | 4/1996 | Picot et al. |
| 5,510,716 | A | 4/1996 | Buffaloe, IV |
| 5,554,805 | A | 9/1996 | Bahrton |
| 5,644,240 | A | 7/1997 | Brugger |
| 5,685,989 | A | 11/1997 | Krivitski et al. |
| 5,690,115 | A | 11/1997 | Feldman et al. |
| 5,724,982 | A | 3/1998 | Schnurer et al. |
| 5,804,717 | A | 9/1998 | Lucas |
| 5,830,365 | A | 11/1998 | Schneditz |
| 5,861,561 | A | 1/1999 | Van Cleve et al. |
| 5,865,871 | A | 2/1999 | Simundich |
| 6,153,109 | A | 11/2000 | Krivitski |
| 6,167,765 | B1 | 1/2001 | Weitzel |
| 6,217,539 | B1 | 4/2001 | Goldau |

OTHER PUBLICATIONS

Anatole Besarab, et al., The Prevention of Access Failure Pressure Monitoring, Hemodialysis Access, pp. 35–37, 1998.

Steve J. Schwab, et al., Prevention of Hemodialysis Fistula Thrombosis. Early Detection of Venous Stenoses, Kidney International, vol. 36 (1989), pp. 707–711.

Anatole Besarab, et al., Utility of Intra–Access Pressure Monitoring in Detecting and Correcting Venous Outlet Stenosis Prior to Thrombosis, Kidney International, vol. 47 (1995), pp. 1364–1373.

Jeffrey Sands, et al., Hemodialysis Access Flow Measurement Comparison of Ultrasound Dilution and Duplex Ultrasonography, ASAIO Journal, 1996, pp. M899–M901.

Nikolai M. Krivitski, Theory and Validation of Access Flow Measurement by Dilution Technique During Hemodialysis, Kidney International, vol. 48 (1995), pp. 244–250.

Richard E. May, et al., Predictive Measures of Vascular Access Thrombosis: A Prospective Study, Kidney International, vol. 52 (1997), pp. 1656–1662.

Barry S. Stauch, et al., Forecasting Thrombosis of Vascular Access with Doppler Color Flow Imaging, American Journal of Kidney Diseases, vol. XIX, No. 6 (Jun.), 1992, pp. 554–557.

Barry Kirschbaum, et al., Study of Vascular Access Blood Flow by Angiodynography, American Journal of Kidney Diseases, vol. 25, No. 1 (Jan.), 1995; pp. 22–25.

David E. Findlay, et al., Duplex and Color Doppler Sonography of Hemodialysis Arteriovenous Fistulas and Grafts, RadioGraphics, vol. 13, No. 5, Sep., 1993 pp. 983–999.

Jeffrey Sands, The Role of Color–Flow Doppler Ultrasound in the Management of Hemodialysis Accesses, pp. 41–43, 1998.

Thomas A. Depner, In–Line Methods, Hemodialysis Access, pp. 38–39, 1998.

Peter J. Brosman, et al., Access Flow Measurements in Hemodialysis Patients; In Vivo Validation of an Ultrasdound Dilution Technique, Journal of American Society of Neprology, vol. 7, No. 6, 1996, pp. 966–969.

R. M. Lindsay, et al., A Comparison of Methods for the Measurement of Hemodialysis Access Recirculation and Access Blood Flow Rate, ASAIO Journal 1998, pp. 62–67.

C.P. Oates, et al., The Use of a Diasonics DRF400 Duplex Ultrasound Scanner to Measure Volume Flow in Arterio–Venous Fistulae in Patients Undergoing Haemodialysis: An Analysis of Measurement Uncertanties, Ultrasound in Medicine and Biology, vol. 16, No. 6, 1990, pp. 571–579.

Jeffrey Sands, et al., The Effect of Doppler Flow Screening Studies and Elective Revisions on Dialysis Access Failure, ASAIO Journal 1992, pp. M524–M527.

Kenneth S. Kleinman, InGraft Velocimetry: A New Technique to Detect Haodialysis Graft Flow and Venous Stenosis, p. 15 (Date Unknown).

Nikolai M. Krivitski, et al., Development of a Method for Measuring Hemodialysis Access Flow: From Idea to Robust Technology, Seminars in Dialysis, Mar.–Apr. 1998, vol. 11, No. 2, pp. 124–130.

Marla Paun et al., New Ultrasound Approaches to Dialysis Access Monitoring, American Journal of Kidney Diseases, vol. 35, No. 3, Mar. 2000, pp. 477–481.

Keen, M. Preisig, P., and Gotch F. (1987) Non–invasive Quantitative Measurement of Hemodialysis Access Graft (HG) Flow. Abstr. International Congress of Nephrology, p. 148.

Marica Lynne Keen, Evaluation of Blood Flow in Vascular Access Grafts Using The Dopplyer Ultrasonic Flow Detector, University of California, San Francisco, Dec. 31, 1985.

Erjun Wang et al., Predictive Value of Access Blood Flow in Detecting Access Thrombosis, ASAIO Journal 1998, pp. M555–M558.

Thomas A. Depner et al., Pressure Effects on Roller Pump Blood Flow During Hemodialysis, ASAIO Journal 1990, pp. M456–M459.

Anatole Besarab et al., The Relationship of Recirculation to Access Blood Flow, American Journal of Kidney Diseases, vol. 29, No. 2 (Feb.), 1997, pp. 223–229.

Kevin L. Sullivan et al., Hemodynamics of Failing Dialysis Grafts, Radiology, Mar. 1993, pp. 867–872.

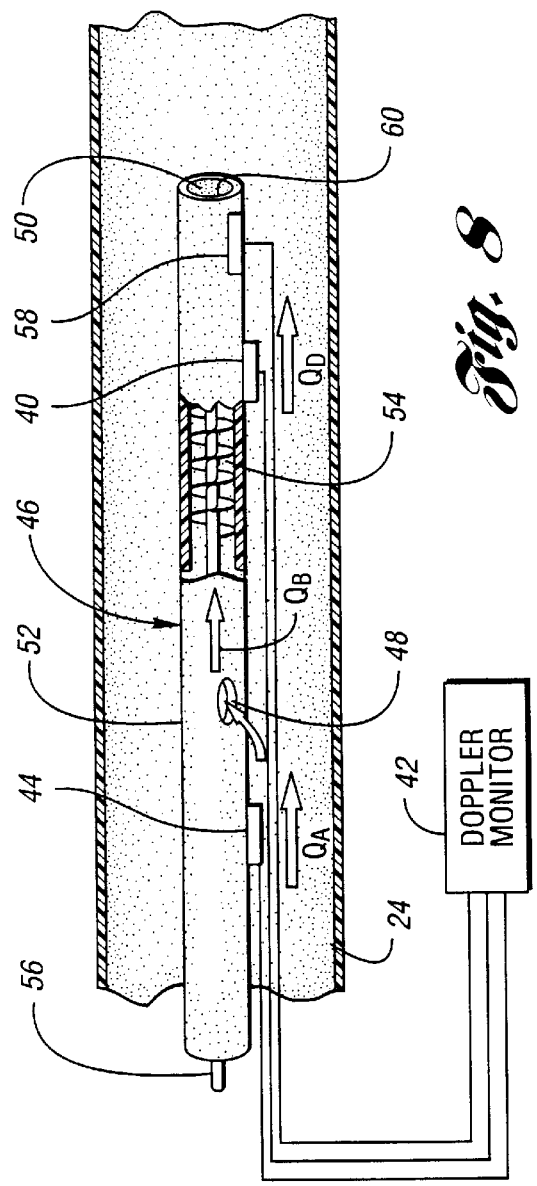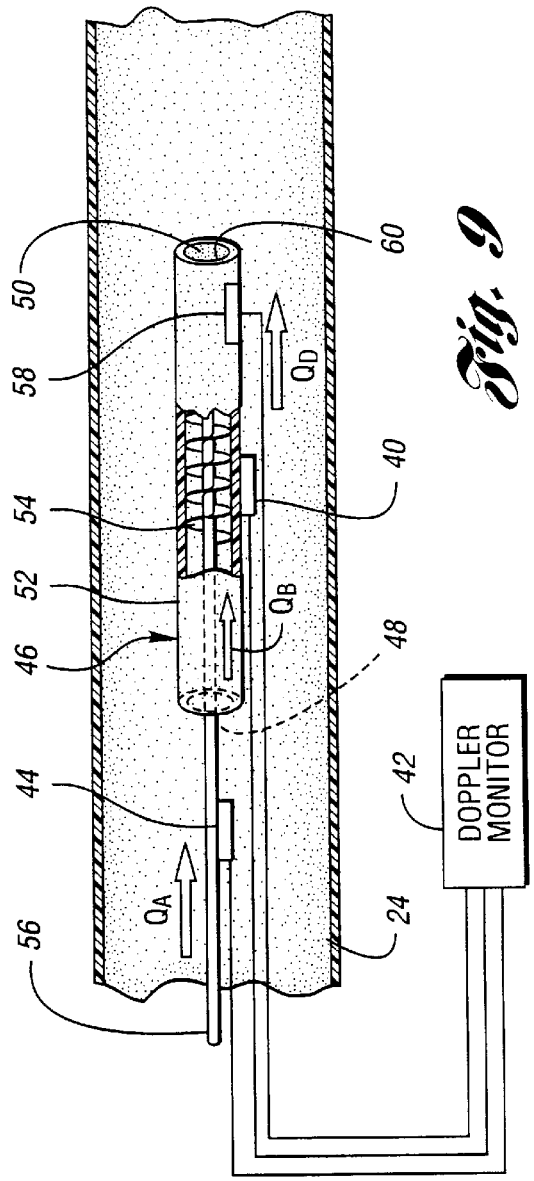

SYSTEM FOR DETERMINING BLOOD FLOW RATE IN A VESSEL USING DIVERTED FLOW MEASUREMENTS

CROSS-REFERENCE TO RELATED APPLICATIONS

This application is a divisional of U.S. application Ser. No. 09/310,673 filed May 12, 1999 now U.S. Pat. No. 6,575,927, which is a continuation-in-part of U.S. application Ser. No. 09/160,685 filed Sep. 25, 1998, now U.S. Pat. No. 6,167,765.

TECHNICAL FIELD

This invention relates to the field of hemodynamics, and more particularly to a system and method for measuring blood flow rate in a vessel, such as a hemodialysis access.

BACKGROUND ART

Hemodialysis is a process by which blood is passed through an external dialysis circuit to replace the function of a patient's kidney. Blood is removed from the patient's vascular system via an arterial line, is passed through a dialysis filter, and is returned to the patient via a venous line. In order to simplify the withdrawal and return of blood, many dialysis patients have an arteriovenous shunt, or access, surgically created between an artery and vein in a location in the body, such as the upper or lower arm. The access provides a permanent site where the arterial line and venous line can be connected to the patient. A vascular access may be constructed from a native arteriovenous fistula, which is a direct connection of a patient's artery to one of his/her veins, or alternatively may be constructed from a synthetic material, typically polytetrafluoroethylene (PTFE).

While a permanent vascular access provides a convenient connection site for arterial and venous lines, malfunction of such an access is a frequent occurrence in patients receiving chronic hemodialysis. Specifically, unpredictable thrombosis and stenosis in an access causes a reduction in blood flow which necessitates correction through angioplasty or other surgical means. If untreated, low blood flow can cause undesired recirculation in the access, where some part of the freshly dialyzed blood from the venous line flows upstream to the arterial line where it is again filtered. Studies have shown that decreased hemodialysis access flow is associated with an increased risk of access thrombosis and stenosis, such that early detection of an access with a low flow rate is essential in order to prevent more serious complications (see May et al., *Kidney Int.* 52: 1656–1662, 1997).

Therefore, the importance of sufficient access blood flow has resulted in the emergence of access surveillance as a necessary component in the care of patients on hemodialysis. Surveillance techniques have been developed to detect low blood flow predictive of future thrombosis and stenosis.

An early method of calculating the access flow rate involves occluding the access, placing a needle into the access to monitor the pressure therein, and pumping blood around the occlusion to determine the relationship between blood flow rate and pressure within the access. This intra-access pressure monitoring may be performed either upstream (see Langescheid et al., *Dialysis and Transplantation* June: 54–55, 1977) or downstream (see Brosman et al., *J. Am. Soc. Nephrol.* 7: 966–969, 1996) from the occlusion. Unfortunately, occlusion of the access may lead to thrombosis, and placement of the needle or pressure sensor within the access is invasive. Static and dynamic venous pressure monitoring, whereby the pressure within the access is measured with the dialysis blood pump off (static) or on (dynamic), have also been used for surveillance (see Besarab et al., *ASAIO J.* Jan–Feb: 35–37, 1998; Schwab et al., *Kidney Int.* 36: 707–711, 1989). However, these methods do not correlate well enough with blood flow rate and lack the sensitivity and specificity needed for accurate access surveillance.

At present, the most reliable methods for surveillance of access blood flow utilize conventional Doppler ultrasound (see Stauch et al., *Am. J. Kidney Dis.* 19: 554–557, 1992; Kirshbaum and Compton, *Am. J. Kidney Dis.* 25: 22–25, 1995; Findley et al., *Radiographics* 13: 983–999, 1993; Sands, *ASAIO J.* Jan–Feb: 41–43, 1998; Oates et al., *Ultrasound Med. Biol.* 16: 571–579, 1990; Sands et al., *ASAIO J.* 38: M524–M527, 1992) or indicator dilution techniques (see Depner, *ASAIO* Jan–Feb: 38–39, 1998; Krivitski, *Kidney Int.* 48: 244–250, 1995; Lindsay et al., *ASAIO J.* Jan–Feb: 62–67, 1998).

To evaluate a vascular access using Doppler ultrasound, an ultrasound unit with both imaging and spectral flow Doppler capabilities, termed duplex ultrasonography, is typically utilized. Access blood flow is calculated using the time-velocity integral of a spectrum obtained from a representative area of the access. The cross-sectional area of the access is measured via imaging, and from these measurements volume blood flow is calculated. However, Doppler ultrasound techniques are fraught with sources of operator error, most often associated with the determination of cross-sectional area as well as assumptions about the velocity profile. In addition, conventional Doppler ultrasound is labor intensive and expensive, such that measurements are not usually made with high enough frequency to effectively monitor the onset of reduced access flow.

Indicator dilution methods have also been utilized to measure access blood flow. U.S. Pat. No. 5,685,989 issued to Krivitski et al. discloses a dilution technique which uses ultrasonic sensors on the arterial and venous lines. For the measurement of access blood flow, the blood lines are reversed and a temporary recirculation is created. Then, a known quantity of an indicator, such as saline, is injected into the venous line. This dilutes the flow of blood in the access, resulting in Doppler velocity changes measured by the ultrasonic sensor on the arterial line. Because this change is proportional to the concentration of injected saline in the blood, access flow can be calculated. The use of other indicator dilution methods to determine blood flow can be found in U.S. Pat. No. 5,312,550 issued to Hester, U.S. Pat. No. 5,510,716 issued to Buffaloe, IV et al., and U.S. Pat. No. 5,644,240 issued to Brugger. Unfortunately, conditions affecting indicator mixing and recirculation of the indicator through the cardiovascular system can affect the accuracy of results using this method. Furthermore, due to the necessity for the reversal of blood lines during dialysis, dilution techniques are cumbersome and time-consuming.

DISCLOSURE OF INVENTION

Therefore, a principal object of the present invention is to provide a system and method for determining the blood flow rate in a vessel.

It is a further object of the present invention to provide a system and method for accurately measuring blood flow rate in a vessel without relying on a measurement of vessel cross-sectional area.

It is another object of the present invention to provide a system and method for determining blood flow rate in a hemodialysis access in a simple, safe, and efficient manner.

Accordingly, a system is provided for determining the performance of a vessel which communicates blood between two locations of a patient. A conduit is provided in fluid communication with the vessel, and has a diversion point for diverting blood from the vessel into the conduit. The system further includes means for determining a flow rate of the diverted blood through the conduit. A first sensor in communication with the vessel generates at least one signal that is a function of a blood flow rate in the vessel downstream from the diversion point, wherein the downstream flow rate depends on the determined conduit flow rate and the performance of the vessel can be determined based on the at least one signal. In addition, a processor can be provided in communication with the first sensor for determining a blood flow rate in the vessel upstream from the diversion point from the at least one signal and the determined conduit flow rate.

Correspondingly, a method is provided for determining the performance of a vessel. The method includes diverting blood from the vessel at a diversion point to obtain a flow of diverted blood in a conduit, and determining a flow rate of the diverted blood through the conduit. The method further includes generating at least one signal correlated with a blood flow rate in the vessel downstream from the diversion point, wherein the downstream flow rate depends on the determined conduit flow rate. Still further, the method includes determining the performance of the vessel based on the at least one signal. In addition, the method can include processing the at least one signal and the determined conduit flow rate to obtain a flow rate in the vessel upstream from the diversion point.

In one embodiment of the present invention, the vessel is a hemodialysis access, and the conduit comprises an external dialysis circuit. Alternatively, the conduit may comprise an intravascular catheter provided with either an intravascular or extravascular pump. In a preferred embodiment of the present invention, the first sensor is an ultrasonic sensor, the ultrasonic sensor directs an unfocused ultrasound beam at the vessel, and the signal represents a time-averaged mean Doppler velocity of blood flow. Still further, additional sensors may be employed to provide a measure of the upstream flow rate as well as the conduit flow rate.

The above objects and other objects, features, and advantages of the present invention are more readily understood from a review of the attached drawings and the accompanying specification and claims.

BRIEF DESCRIPTION OF DRAWINGS

FIG. 8 shows an embodiment of the blood flow rate measuring system of FIG. 7 that utilizes an intravascular pump;

FIG. 9 shows an alternative configuration of the blood flow rate measuring system of FIG. 8;

BEST MODE FOR CARRYING OUT THE INVENTION

The present invention provides a system and method for determining the blood flow rate in a vessel, such as a hemodialysis access. Blood flow rate in the vessel is determined by diverting a portion of the blood from the vessel into a conduit, such as an external dialysis circuit, and applying the principle of conservation of mass. The flow rate in the vessel downstream from the conduit is observed for at least one flow rate generated in the conduit. The relationship between the downstream vessel flow rate and the conduit flow rate can then be used to calculate the blood flow rate in the vessel upstream from the conduit, which represents the net vessel flow rate. Depending on the location and nature of the vessel, net vessel flow rate can indicate such clinically important measures as the functionality of a hemodialysis access, the cardiac output, or the blood being delivered to an extremity.

Figure 1:
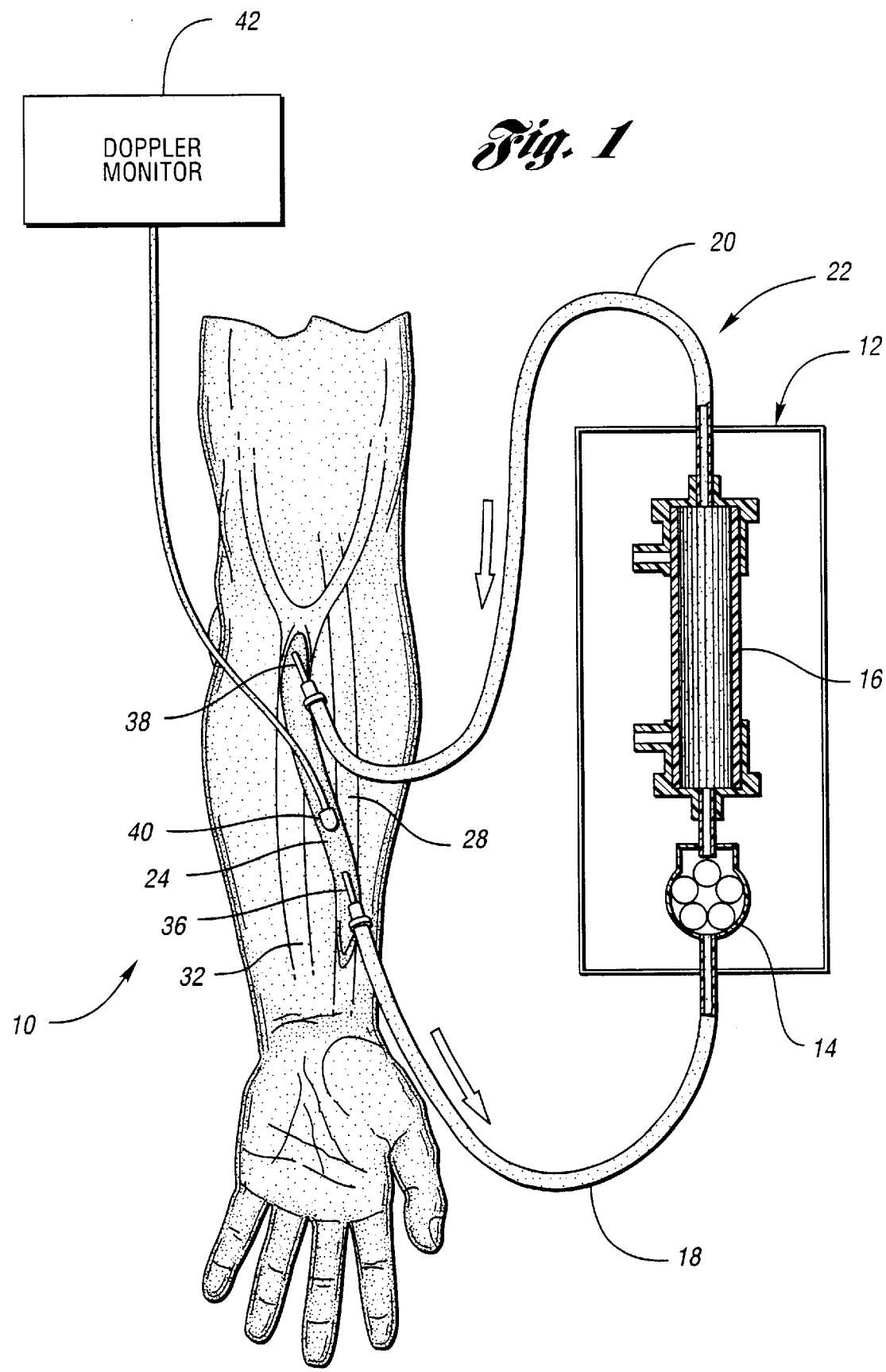
FIG. 1 illustrates a hemodialysis system in accordance with the present invention.
Figure 2:
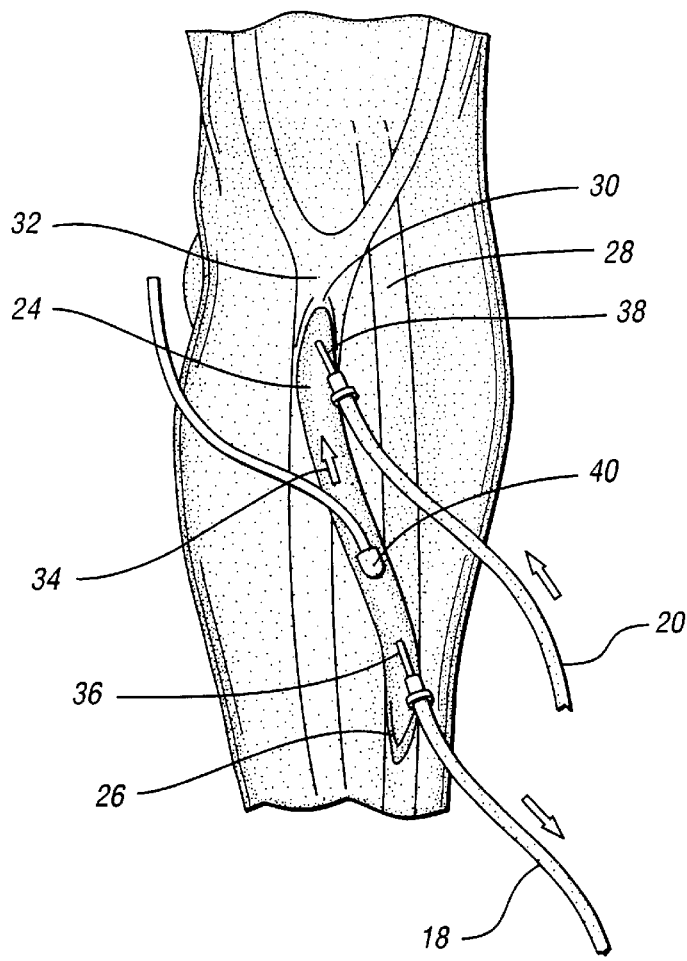
FIG. 2 is an enlarged view of the connections to a hemodialysis access within the system of FIG. 1.

In accordance with the present invention, a hemodialysis system is provided which is designated generally by reference numeral 10 in FIG. 1. Hemodialysis system 10 comprises conventional dialysis equipment 12, including a dialysis pump 14 and filter 16. Dialysis equipment 12 is provided on one end with an arterial line 18 and on the other end with a venous line 20, each constructed of sterile tubing. Arterial line 18, dialysis equipment 12, and venous line 20 form an external dialysis circuit, denoted by reference numeral 22. To perform hemodialysis, dialysis circuit 22 is connected to a patient's vessel, which is depicted in FIG. 1 as an arteriovenous shunt, or access 24. As best shown in FIG. 2, access 24 has a first end 26 connected to a patient's artery 28 and a second end 30 connected to a patient's vein 32. Access 24 may be an artificial subcutaneous vessel, such as a polytetrafluoroethylene (PTFE) graft, or a native fistula that is surgically created between artery 28 and vein 32. The normal direction of blood flow in access 24 is indicated by arrow 34.

Referring again to FIGS. 1 and 2, access 24 has two needles introduced into its lumen during dialysis, an arterial needle 36 connected to arterial line 18 and a venous needle 38 connected to venous line 20 for the return of blood to access 24. Blood is diverted into dialysis circuit 22 through arterial needle 36, flows through arterial line 18 to venous line 20 while being propelled by pump 14 at a conduit flow rate, and is returned to access 24 via venous needle 38. According to the invention, a first sensor 40 is provided in communication with access 24 to generate a signal correlated with the blood flow rate downstream from arterial needle 36 during dialysis. While first sensor 40 is preferably located downstream from arterial needle 36, more specifically between arterial needle 36 and venous needle 38, it is understood that first sensor 40 may be located anywhere suitable for detecting the downstream flow rate. Referring to hemodialysis system 10 depicted in FIG. 1, first sensor 40 would typically be secured to the skin of the patient's lower arm overlying access 24.

In some cases, needles 36 and 38 are located far enough apart and oriented in such a way that first sensor 40 may be easily placed between them. Other times, there is little distance between arterial needle 36 and venous needle 38 in which to place first sensor 40. Since flow in the vicinity of either arterial needle 36 or venous needle 38 will typically be turbulent, first sensor 40 is preferably placed at a sufficient distance from either needle 36 or 38, on the order of 1 cm, to avoid the turbulent flow and obtain a more accurate signal. Since needles 36 and 38 are often oriented in the direction of access flow, placement of first sensor 40 close to venous needle 38 will typically accomplish this goal. With this orientation, flow will be moving away from first sensor 40, allowing signal detection from areas of turbulent flow to be minimized. Such placement of first sensor 40 near or under venous line 20 is facilitated if first sensor 40 is constructed to be small and have a low profile. In addition, if first sensor 40 is located in proximity to either arterial 36 or venous needle 38, then first sensor 40 is preferably directed away from the tips of needles 36, 38, regardless of whether needles 36, 38 are oriented upstream or downstream.

In a preferred embodiment, first sensor 40 comprises an ultrasonic sensor, and the signal generated by first sensor 40 comprises a Doppler ultrasound signal relating to the blood flow in access 24. Doppler ultrasound signal characteristics include the maximum signal, minimum signal, signal amplitude, and time-averaged mean signal, and each are related to blood flow rate and will vary according to blood flow rate. Of these characteristics, the most accurate correlate with blood flow rate is thought to be the time-averaged mean signal, more particularly the time-averaged mean velocity, and this is the characteristic of the Doppler ultrasound signal which is preferably utilized in practicing the method of the present invention. However, it is understood that the present invention may utilize a measurement of any variable that relates predictably to volume flow rate, as will be explained below.

As shown in FIG. 1, first sensor 40 is connected to a signal monitor, preferably a Doppler velocity monitor 42. For example, a suitable Doppler velocity monitor would be Model 1052-C Vascular Mini-Lab manufactured by Parks Medical Electronics, Inc. (Aloha, Oreg.). In operation, first sensor 40 sends an ultrasound beam through the blood passing through access 24, and generates an output signal proportional to the time-averaged mean Doppler velocity of the blood therein. In a preferred embodiment, an unfocused ultrasound beam is utilized in order to insonify as much of access 24 as possible. Use of an unfocused beam could potentially increase the accuracy of measurements by increasing signal sampling within access 24.

While the present invention is described in the context of the ultrasound instrumentation described above, it is understood that the method of the present invention could be performed equally as well using other devices such as a magnetic resonance imaging (MRI) system, an electromagnetic blood flow meter, an intra-access pressure sensor, or other devices relating to flow measurement.

Access 24 has a blood flow rate dependent on numerous factors including systemic blood pressure, pre- and post-access geometry, and fluid viscosity. Referring now to the schematic diagram of FIG. 3, the net access blood flow rate, either upstream from arterial needle 36 or downstream from venous needle 38, can be labeled $Q_A$. Access flow between arterial 36 and venous 38 needles will decrease during dialysis as a function of the blood diverted through dialysis circuit 22 at the conduit flow rate $Q_B$ controlled by pump 14. Assuming that the net flow through the system does not change during dialysis, the flow rate between needles 36 and 38 in access 24 during dialysis, denoted as $Q_D$, will follow the relationship $$Q_D + Q_B = Q_A \tag{1}$$

or $$Q_D = Q_A - Q_B \tag{2}$$

In certain prior art methods, $Q_A$ is determined by measuring the velocity of blood flow in access 24 and multiplying this velocity by a measurement of the cross-sectional area of access 24. Because of the many factors involved in estimating an accurate access cross-sectional area and an accurate distribution of velocities through that area, the method of the present invention uses the relationship of equation (1) to independently derive the blood flow $Q_A$ as follows.

Figure 3:
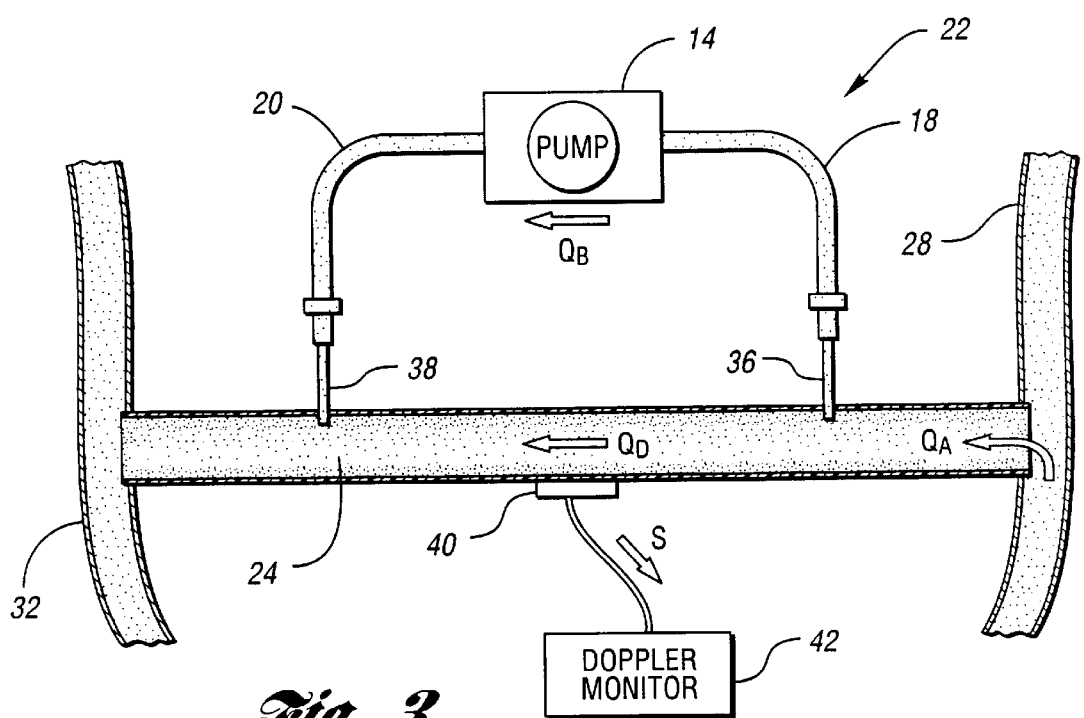
FIG. 3 is a schematic representation of the hemodialysis system of FIG. 1.
Figure 4:
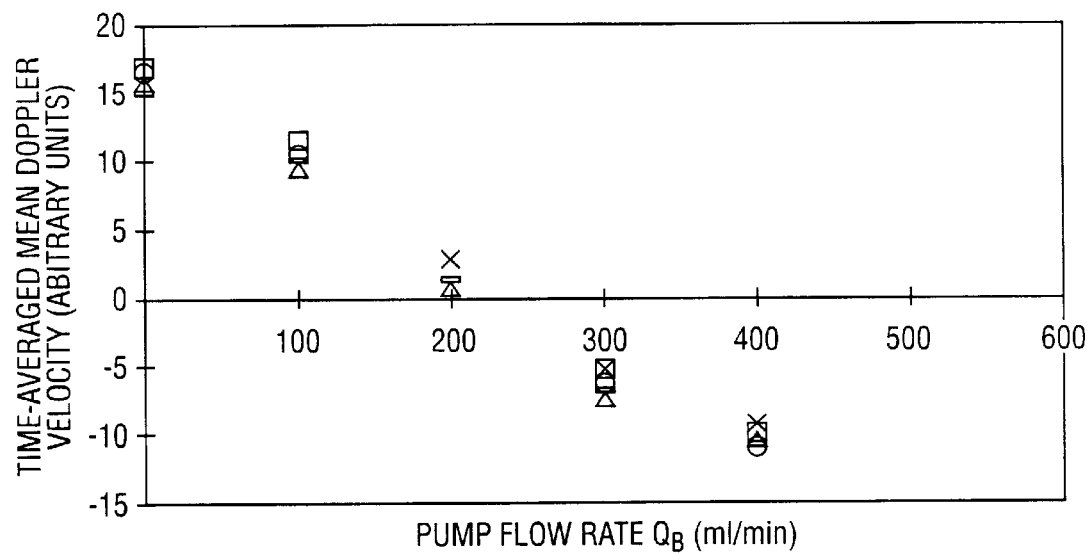
FIG. 4 is a graph depicting the linear relationship between the Doppler velocity signal and the dialysis pump flow rate.

First sensor 40 is located between arterial 36 and venous 38 needles as illustrated in FIG. 3, and the ultrasound signal generated by first sensor 40 is denoted as S. S is measured for at least two different values of $Q_B$ by varying the speed of dialysis pump 14. $Q_B$ is typically determined simply by reading an indicator on pump 14. An example of the relationship between the signal S, in this case the time-averaged mean Doppler velocity, and the pump flow rate $Q_B$ is shown in the graph of FIG. 4. From these data, a modeling function is constructed for the signal S, where $S=f(Q_B)$. This modeling function may take the form of any one-to-one function, such as a linear, polynomial, or exponential function. As shown in FIG. 4, the time-averaged mean Doppler velocity signal has a tight, linear relationship to the flow $Q_B$, such that a linear regression function can be calculated.

Assuming a constant $Q_A$, $Q_D$ will decrease with increasing $Q_B$ such that the signal $S=f(Q_B)$ will decrease, as shown in FIG. 4. As $Q_D$ approaches zero, S will approach zero or a known value for S that corresponds to zero blood flow $Q_D$. This value for signal S is designated as $S_0$. The value for $S_0$ corresponds to the value for $Q_B=Q_A$ since $Q_D=0$, as dictated by equations (1) and (2). Accordingly, $Q_B$ at the value $Q_A$ can be solved for graphically (the x-intercept) or by determining the inverse of the modeling function for S, namely $Q_B=f^{-1}(S)$. Then, setting $S=S_0$ yields the value for which $Q_B$ would equal $Q_A$, namely $Q_A=f^{-1}(S_0)$. Therefore, the modeled function derived from the signal S and knowledge of the blood flow rate $Q_B$ through dialysis circuit 22 allows determination of the flow rate $Q_A$ in access 24. It is understood that this method may be used to determine $Q_A$ regardless of whether $Q_A$ is less than, greater than, or equal to $Q_B$.

When employing the method of the present invention, the accuracy of the measurement of the signal S, and therefore the measurement of $Q_A$, is improved if the flow rate $Q_B$ through dialysis circuit 22 can be increased. Typical flow rates for dialysis pumps 14 range only from 0 ml/min to 400 ml/min, which is usually lower than the flow rate $Q_A$ during dialysis. However, if $Q_B$ can be increased temporarily, the resulting two measurements of S obtained will vary greatly, thereby improving the accuracy of the modeling function in determining $Q_A$.

Figure 10:
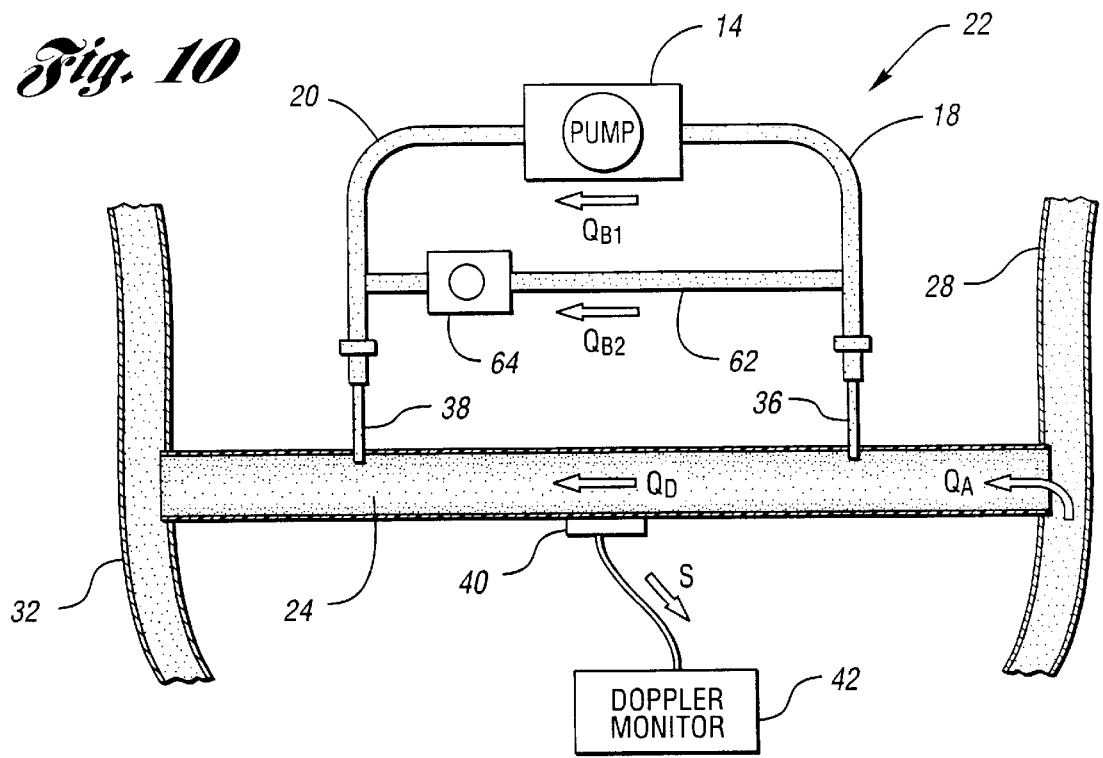
FIG. 10 shows an embodiment of the blood flow rate measuring system of the present invention that incorporates an additional blood line.

In order to increase $Q_B$ temporarily, an additional blood line 62 can be employed to bridge dialysis circuit 22 from arterial line 18 to venous line 20, thereby creating a separate flow path as shown in FIG. 10. With this configuration, the flow rate through the normal dialysis circuit 22 is designated $Q_{B1}$ while $Q_{B2}$ represents the flow rate in additional blood line 62. The flow $Q_{B2}$ can be controlled passively, by making additional line 62 of lower resistance than normal dialysis circuit 22. A regulator, such as a stopcock (not shown), could then be used to vary the resistance in additional line 62 in order to regulate the flow rate $Q_{B2}$. Alternatively, the flow $Q_{B2}$ can be controlled actively, by using a pump 64 in additional line 62 to divert blood therethrough. In either case, a flow monitor (not shown) is preferably used to accurately measure $Q_{B2}$. Then, $Q_{B1}$ is preferably set equal to zero, or alternatively to any other known flow rate, and S is measured and used to determine $Q_A$.

In an alternative embodiment of the present invention, a number of different measurements of the signal S are performed at a number of different blood flow rates $Q_B$. The repeated measurements allow for the reliability of the modeling function to be determined, such as by using linear regression and calculating a correlation coefficient, to reflect how accurately the modeling function represents the measurements collected for signal S.

Although the method of the present invention has been described above as utilizing two or more measurements of the signal S to determine $Q_A$, only one measurement of S is required to determine $Q_A$ when $Q_A$ is less than the maximum blood flow rate $Q_B$ through dialysis circuit 22. This measurement value of S corresponds to the circuit flow rate $Q_B$ where the downstream flow rate $Q_D$ is zero, such that $Q_B = Q_A$. Therefore, the speed of pump 14 may be increased to the value where the downstream signal S is zero in order to determine the value of $Q_A$ where $Q_A = Q_B$ with only one measurement. Even if S is not exactly zero, but is near zero or small relative to other signals, $Q_A$ may be approximated with respect to $Q_B$ using the above method.

Of particular note is the advantage that the system and method of the present invention do not require the magnitude of the cross-sectional area of access 24 to determine the flow $Q_A$. In fact, since the signal S is measured in arbitrary units, the absolute magnitude of the velocity of flow within access 24 is not necessary to accurately calculate access flow $Q_A$. As stated previously, the only requirement for the signal S is that it have a one-to-one relationship with $Q_B$, a requirement that is satisfied by the time-averaged mean Doppler velocity.

In addition to the access flow measurements determined by the system and method of the present invention, the periodic nature of the Doppler flow patterns through access 24 during the cardiac cycle may be observed as the speed of pump 14 is varied. In patients with lower access volume flow rates, periods of low, zero, and reversed Doppler velocity frequently occur during diastole as the speed of pump 14 is increased, even though forward flow is maintained during systole. This periodic forward and reverse flow during the cardiac cycle occurs as a result of increased flow into access 24 during systole which temporarily exceeds the flow diverted through dialysis circuit 22, followed rhythmically by comparatively low flow into access 24 during diastole which is exceeded by the conduit flow rate resulting in reversed flow in the access during diastole alone. Using the system and method of the present invention, low, zero, and even reversed diastolic flow in access 24 can be detected even though the net flow through access 24 is still forward as described below.

Since the blood flow rate $Q_A$ through access 24 varies with systole and diastole in the cardiac cycle, components of the signal S can give information to calculate other values of clinical interest. For example, instantaneous volume flow $Q_A$ in access 24 is higher during systole than diastole. The corresponding signal S will therefore show the same relationship since S is related to volume flow as described previously. For example, let $S_{min}$ represent the component of the signal S corresponding to a minimum flow rate $Q_{Amin}$ during diastole. $S_{min}$ can be measured at different values of $Q_B$ and a modeling function can be determined to calculate $Q_{Amin}$. When $Q_{Amin}$ is less than $Q_B$ such that $S_{min}=0$, the diastolic flow $Q_{Amin}$ in access 24 may be determined using only one measurement. As above, $Q_{Amin}$ can be approximated with a single measurement if the diastolic signal $S_{min}$ is near zero at a given blood flow rate $Q_B$. In a similar fashion, systolic flow, the difference between systolic and diastolic flow, or other derived parameters may be determined by selecting a component or components of S and calculating a modeling function to determine the particular volume flow. In this way, the instantaneous volume flow throughout the cardiac cycle can be determined.

In fact, judgements about the access flow rate $Q_A$, and therefore the performance of access 24, can be made by merely observing the downstream flow rate $Q_D$ at a given flow rate $Q_B$ without actually calculating $Q_A$. For example, when the flow $Q_A$ in access 24 is on the order of, but still greater than, the flow $Q_B$, $S_{min}$ will be near zero. Therefore, the diastolic flow $Q_{Amin}$ in the access 24 is known to be approximately equal to $Q_B$ by simple inspection of the signal $S_{min}$ at a single $Q_B$ without making any calculation of $Q_A$. In addition, since the signal S will vary in a periodic manner throughout the cardiac cycle, information about $Q_A$ can be ascertained by observing the signal S over time. If S is at times above zero, such as during systole, and at times below zero, such as during diastole, then it is known through observation of this signal that the access flow $Q_A$ is greater than $Q_B$ during systole and less than $Q_B$ during diastole. If S always remains less than zero, then it can be concluded that the access flow $Q_A$ is less than $Q_B$ throughout the cardiac cycle.

Similarly, judgements about the access flow $Q_A$ and performance of access 24 can be made by observation of the signal S as $Q_B$ is varied, without measuring the signal exactly. For example, S may be observed in real time as $Q_B$ is varied over a range large enough to observe the degree of change in $Q_D$. For example, suppose that the flow $Q_A$ in access 24 is a typical "lower" access flow of about 700 ml/min, and that $Q_B$ is varied from 400 ml/min to 100 ml/min and back to 400 ml/min as S is observed over time. Since $Q_D=Q_A-Q_B$, $Q_D$ will vary from 300 ml/min to 600 ml/min and back to 300 ml/min as $Q_B$ is varied, such that a 100% change in S will be observed. In contrast, if $Q_A$ is a typical "higher" access flow of approximately 2,000 ml/min, then $Q_D$ will vary from 1600 to 1900 ml/min, resulting in a 19% change in signal amplitude, when $Q_B$ is varied between the same flow rates as above. Thus, by simple inspection of the change S over time, "low" and "high" flow rates for $Q_A$ can be distinguished without specifically calculating its value.

A special case exists when the access blood flow $Q_A$ varies with the flow $Q_B$ for different speeds of dialysis pump 14. As blood is diverted through dialysis circuit 22, pressure within access 24 may fall and $Q_A$ may therefore increase as conduit flow rate $Q_B$ increases. The present invention provides the following system and method which correct for any dependence of $Q_A$ on $Q_B$ assuming that the signal S varies substantially linearly with volume flow, as is the case with time-averaged mean Doppler velocity. As above, the blood flow between arterial 36 and venous 38 needles is defined as $Q_D=Q_A-Q_B$. $Q_A(Q_B)$ designates the function $Q_A$ for each conduit flow rate $Q_B$, since $Q_A$ is postulated to change with each change in $QB_B$.

Figure 5:
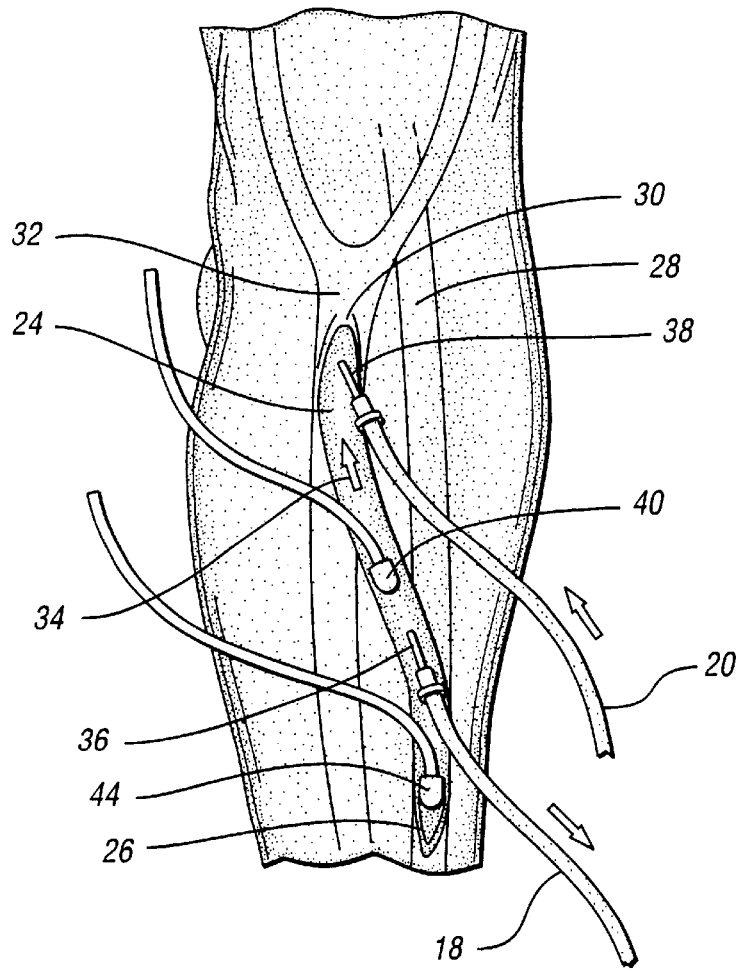
FIG. 5 depicts an alternative monitoring configuration of the hemodialysis access within the system of FIG. 1.
Figure 6:
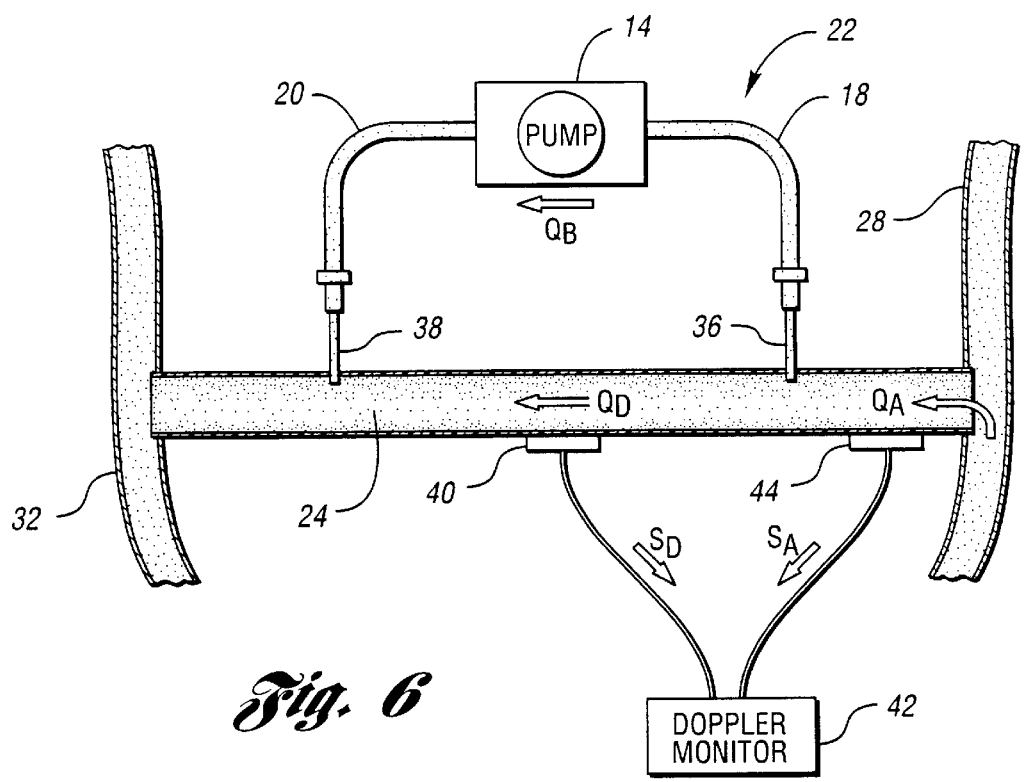
FIG. 6 is a schematic representation of a hemodialysis system configured as in FIG. 5.

Referring now to FIGS. 5 and 6, $S_D$ is defined to be the signal provided by first sensor 40 located between arterial 36 and venous 38 needles corresponding to the flow $Q_D$. In this embodiment of the invention, a second sensor 44, preferably located upstream from arterial needle 36, provides a signal $S_A$ corresponding to access flow $Q_A$. These signals are assumed to vary with $Q_B$, giving $S_D(Q_B)$ and $S_A(Q_B)$ for each pump flow rate $Q_B$. Given this dependence on $Q_B$, $S_D$ and $S_A$ correspond to the same blood flow rate when $Q_B=0$. Therefore, $S_A$ can be multiplied by a constant to give $S_A{}'$ that will equal $S_D$ when $Q_B=0$, or $$S_A{}'(0)=C*S_A(0)=S_D(0) \quad (3)$$

where $C=S_D(0)/S_A(0)$. Accordingly, the signal $S_A{}'$ will correspond to the increase in $Q_A$ with increasing $Q_B$. Referring to equation (2), $Q_D$ will fall with increasing $Q_B$ by the amount $Q_B$ less the increase in inflow $Q_A(Q_B)-Q_A(0)$ Subtracting the corresponding change in signal $S_A{}'(Q_B)-S_A{}'(0)$ from $S_D$ gives a correction allowing one to solve for $Q_A$.

If a corrected $Q_A$ is to be determined during dialysis, when the value of $Q_B$ will be greater than 0 ml/min, a modified version of the above method can be employed. Using this modified method, the fractional change in $Q_A$ can be determined as $Q_B$ is varied from a first value, $Q_{B1}$ (for example, 0 ml/min), to a second value, $Q_{B2}$ (for example, 400 ml/min). First, the volume flow $Q_A$ is equal to:

$$Q_A=v*A \quad (4)$$

where v is the mean velocity in access 24 and A is the cross-sectional area of access 24. Equation (4) is equivalent to:

$$Q_A=S_A*C*A \quad (5)$$

where $S_A$ is the signal corresponding to access flow $Q_A$, and C is a constant that is adjusted for factors such as sensor orientation. Then, the fractional change in $Q_A$, as a function of the blood flow rate $Q_B$, as $Q_B$ is varied from $Q_{B1}$ to $Q_{B2}$ is:

$$Q_A(Q_{B2})/Q_A(Q_{B1})=S_A(Q_{B2})*C*A/S_A(Q_{B1})*C*A \quad (6)$$

or $$Q_{A2}/Q_{A1}=S_{A2}*C*A/S_{A1}*C*A \quad (7)$$

Since C and A do not change as $Q_B$ is varied from $Q_{B1}$ to $Q_{B2}$, equation (7) becomes:

$$Q_{A2}/Q_{A1}=S_{A2}/S_{A1} \quad (8)$$

Incorporating the example values for $Q_{B1}$ and $Q_{B2}$ and rearranging, equation (8) becomes:

$$Q_A(400)=S_A(400)/S_A(0)*Q_A(0) \quad (9)$$

Therefore, if $Q_A(0)$ is determined, that blood flow rate can be multiplied by the fractional change ratio to determine the blood flow rate through access 24 during dialysis at some value (e.g. 400 ml/min) of $Q_B$. It should be noted that in carrying out this method, first sensor 40 is not required.

In an alternative embodiment of the present invention, external dialysis circuit 22 is not a required component of the system for measuring the blood flow rate in vessel 24. In the embodiments shown in FIGS. 7–9, an intravascular catheter 46 provided with either an extravascular or intravascular pump is placed in vessel 24. The blood flow through any vessel 24 can be measured with catheter 46 using the same equations and relationships described previously. For instance, catheter 46 could be placed in the pulmonary artery to measure cardiac output, or in the superior or inferior vena cavae to measure venous return. Alternatively, catheter 46 could be combined with a left or right ventricular assist device to monitor the function thereof.

Figure 7:
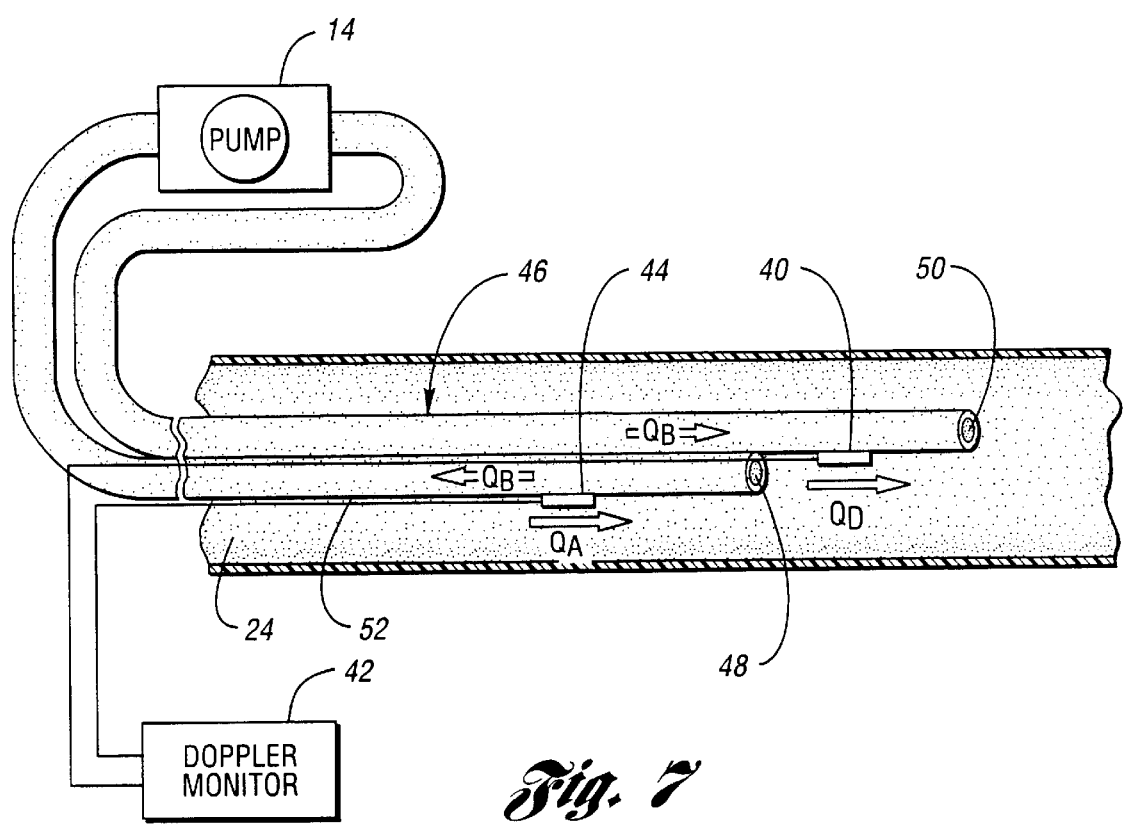
FIG. 7 shows an intravascular catheter embodiment of the blood flow rate measuring system of the present invention.

In the embodiment shown in FIG. 7, catheter 46 is depicted as a conventional dual lumen catheter having an inlet 48 which allows blood to be diverted from vessel 24 and into catheter 46. Blood travels through catheter 46 at a flow rate $Q_B$ generated by an extravascular pump (not shown) similar to dialysis pump 14, and is returned to vessel 24 through an outlet 50. However, it should be understood that the return of blood to vessel 24 via outlet 50 is not required to carry out the method of the present invention. First sensor 40 is preferably affixed to an outside surface 52 of catheter 46 downstream from inlet port 48, more specifically between inlet 48 and outlet 50, to generate the signal $S_D$ corresponding to the flow $Q_D$ as it varies with different flow rates $Q_B$. Optionally, second sensor 44 may be affixed to outside catheter surface 52 upstream from inlet port 48 to provide a measure of $Q_A$ and any dependence thereof on $Q_B$. Of course, sensors 40 and 44 may be located anywhere suitable for detecting flows $Q_D$ and $Q_A$, respectively.

In the embodiment depicted in FIG. 8, catheter 46 is shown as a single lumen catheter which incorporates an intravascular pump 54 to generate $Q_B$. Pump 54 may be of a screw, peristaltic, occluding, or any other type. Pump 54 is driven by a drive line 56 which extends through catheter 46 and is connected to an external motor (not shown). In addition to first 40 and second 44 sensors, a third sensor 58 may optionally be affixed to an inside surface 60 of catheter 46 to provide an independent measure of $Q_B$. In an alternative embodiment shown in FIG. 9, catheter 46 is constructed as a cylindrical housing which does not extend extravascularly, and optional second sensor 44 is affixed to drive line 56.

Figure 11:
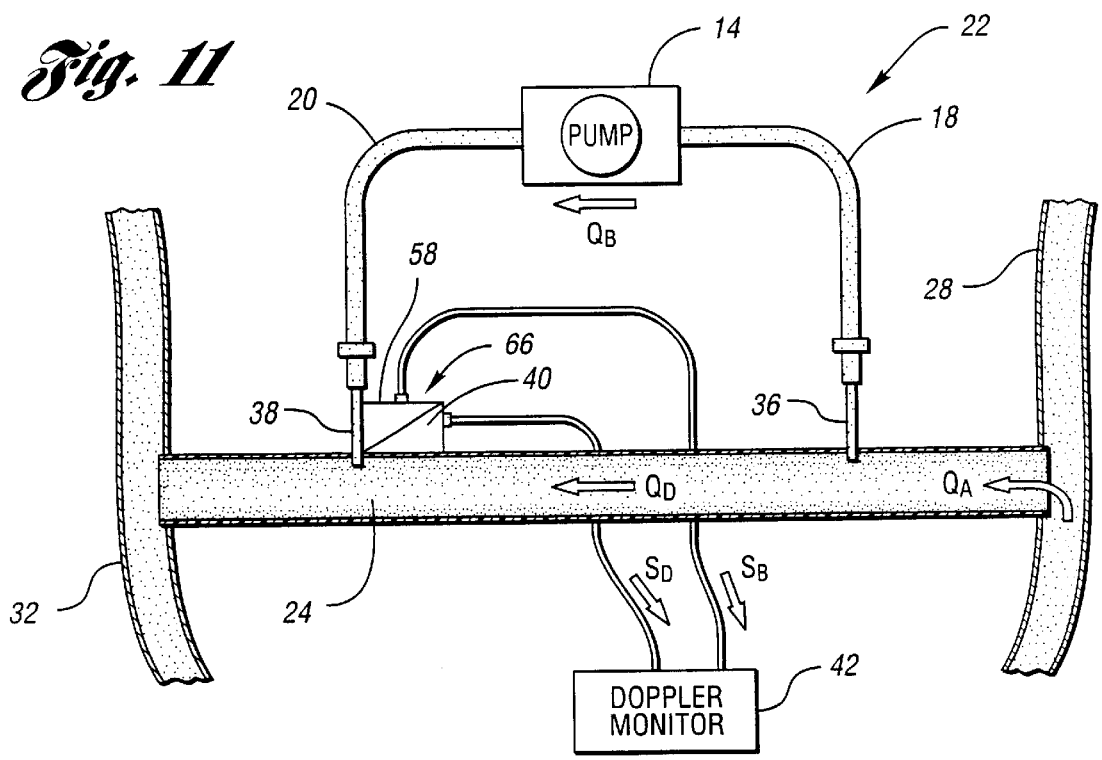
FIG. 11 depicts another alternative monitoring configuration of the hemodialysis access within the system of FIG. 1.

Since dialysis pump speed indicators can vary from true dialysis circuit flow rates $Q_B$, third sensor 58 can be used in conjunction with external dialysis circuit 22 to measure the flow $Q_B$ directly instead of relying on a reading from dialysis pump 14. Referring now to FIG. 11, third sensor 58 could be located anywhere along arterial 18 or venous line 20, or along arterial 36 or venous needle 38. Referring to equation (4) above, $Q_B=v*A$, where v is the velocity and A is the cross-sectional area. Since A is known for each of arterial and venous lines 18, 20 and arterial and venous needles 36, 38 and the signal detected by third sensor 58 is representative of the velocity, $Q_B$ for any part of circuit 22 can be calculated easily. As shown, third sensor 58 can even be located in close proximity to or within the same housing as first sensor 40. Using the latter configuration, the combined housing 66 would need to be positioned between arterial needle 36 and venous needle 38 so that, by sending ultrasound beams in opposite directions, signals could be obtained from both circuit 22 and access 24.

As an extension of the method presented above, it may be possible to simultaneously measure $Q_B$ and $Q_D$ with a single sensor. The sensor would preferably be located over venous needle 38 in a position to insonify both venous needle 38 and access 24 simultaneously with one ultrasound beam. Since the cross-sectional area of needle 38 is small, the flow velocity in needle 38 will be high. In contrast, the velocity in access 24 will be lower due to its comparatively larger cross-sectional area, and will also vary in a periodic manner with systole and diastole. Using an appropriate algorithm, the combined signal from the sensor could be decomposed into these two separate velocity signals. Once the values for the two velocities were obtained, $Q_B$ could be calculated by multiplication with the known cross-sectional area of needle 38, and $Q_D$ could be calculated by the methods described herein.

It is understood, of course, that while the form of the invention herein shown and described constitutes a preferred embodiment of the invention, it is not intended to illustrate all possible forms thereof. For example, the system and method of the present invention may be practiced using body fluids other than blood. Furthermore, the invention may be utilized for purposes ancillary to the measurement of blood flow rate in a vessel. It will be understood that the words used are words of description rather than limitation, and that various changes may be made without departing from the spirit and scope of the invention disclosed.

What is claimed is:

1. A system for determining the performance of a vessel which communicates blood between two locations of a patient, comprising:
   a conduit in fluid communication with the vessel, the conduit having a diversion point from which blood is diverted from the vessel into the conduit, wherein the vessel has a blood flow rate $Q_A$ upstream from the diversion point and a blood flow rate $Q_D$ downstream from the diversion point;
   means for determining a flow rate $Q_B$ of the diverted blood through the conduit; and
   a first sensor in communication with the vessel for generating at least one signal that is a function of the downstream flow rate $Q_D$ without requiring a cross-sectional area of the vessel, wherein the downstream flow rate $Q_D$ depends on the determined conduit flow rate $Q_B$ and the upstream flow rate $Q_A$, such that the performance of the vessel can be determined by observing the at least one signal to obtain information about the upstream flow rate $Q_A$.

2. The system of claim 1, further comprising a processor in communication with the first sensor for determining the upstream flow rate $Q_A$ from the at least one signal and the conduit flow rate $Q_B$.

3. The system of claim 2, further comprising a second sensor in communication with the vessel and the processor to generate at least one signal correlated with the upstream flow rate $Q_A$.

4. The system of claim 2, further comprising a third sensor in communication with the conduit and the processor to generate at least one signal correlated with the conduit flow rate $Q_B$.

5. The system of claim 4, wherein the third sensor is disposed in a combined housing with the first sensor.

6. The system of claim 1, wherein the vessel comprises a hemodialysis access.

7. The system of claim 1, further comprising a pump for diverting blood into the conduit.

8. The system of claim 1, wherein the conduit further comprises a return point from which blood is returned into the vessel from the conduit.

9. The system of claim 8, wherein the conduit comprises an external dialysis circuit.

10. The system of claim 8, wherein the first sensor is spaced from the diversion point and the return point in order to avoid turbulent flow.

11. The system of claim 8, wherein the first sensor is directed away from the diversion point and the return point.

12. The system of claim 1, wherein the first sensor includes an ultrasonic sensor.

13. The system of claim 12, wherein the ultrasonic sensor directs an unfocused ultrasound beam at the vessel.

14. The system of claim 1, wherein the at least one signal represents a time-averaged mean Doppler velocity.

15. The system of claim 1, wherein the conduit comprises an intravascular catheter.

16. The system of claim 1, wherein the first sensor is operable to generate the at least one signal for observing flow characteristics in the vessel throughout a cardiac cycle.

17. The system of claim 1, wherein the first sensor is operable to generate the at least one signal for observing flow characteristics in the vessel during diastole.

18. The system of claim 1, wherein the first sensor is operable to generate the at least one signal for observing flow characteristics in the vessel during systole.

19. The system of claim 1, wherein the first sensor is operable to generate the at least one signal for observing flow characteristics in the vessel as the conduit flow rate $Q_B$ is varied.

20. The system of claim 1, further comprising an additional line that bridges the conduit to create a separate flow path with a separate, additional line blood flow rate.

21. The system of claim 20, wherein the additional line has a lower resistance than the conduit.

22. The system of claim 20, further comprising a pump in fluid communication with the additional line to regulate the additional line blood flow rate.

23. The system of claim 20, further comprising a flow monitor in communication with the additional line to measure the additional line blood flow rate.

24. A system for determining blood flow rate in a vessel which communicates blood between two locations of a patient, comprising:
   a conduit in fluid communication with the vessel, the conduit having a diversion point from which blood is diverted from the vessel into the conduit, wherein the vessel has a blood flow rate $Q_A$ upstream from the diversion point and a blood flow rate $Q_D$ downstream from the diversion point;
   an indicator for determining a flow rate $Q_B$ of the diverted blood through the conduit;
   a first sensor in communication with the vessel for generating at least one signal that is a function of $Q_D$ without requiring a cross-sectional area of the vessel, wherein $Q_D$ depends on $Q_B$ and $Q_A$; and
   a processor in communication with the first sensor for processing the at least one signal and $Q_B$ to obtain $Q_A$.

25. The system of claim 24, further comprising a second sensor in communication with the vessel and the processor to generate at least one signal correlated with $Q_A$.

26. The system of claim 24, further comprising a third sensor in communication with the conduit and the processor to generate at least one signal correlated with $Q_B$.

27. The system of claim 24, wherein the vessel comprises one of a hemodialysis access and an intravascular catheter.

28. The system of claim 24, wherein the conduit comprises an external dialysis circuit.

29. The system of claim 24, further comprising a pump for diverting blood into the conduit.

30. The system of claim 24, wherein the first sensor includes an ultrasonic sensor.

31. The system of claim 24, further comprising an additional line that bridges the conduit to create a separate flow path with a separate additional line blood flow rate, the additional line having a lower resistance than the conduit.

32. A system for determining blood flow rate in a vessel which communicates blood between two locations of a patient, comprising:
   a conduit in fluid communication with the vessel, the conduit having a diversion point from which blood is diverted from the vessel into the conduit and a return point from which blood is returned into the vessel from the conduit, wherein the vessel has a blood flow rate $Q_A$ upstream from the diversion point and a blood flow rate $Q_D$ downstream from the diversion point;

a pump for diverting blood from the vessel into the conduit;

means for determining a flow rate $Q_B$ of the diverted blood through the conduit;

a first sensor in communication with the vessel for generating at least one signal that is a function of $Q_D$ without requiring a cross-sectional area of the vessel, wherein $Q_D$ depends on $Q_B$ and $Q_A$; and a processor in communication with the first sensor for processing the at least one signal and $Q_B$ to obtain $Q_A$.

* * * * *